(12) United States Patent
Bos

(10) Patent No.: US 8,685,944 B2
(45) Date of Patent: Apr. 1, 2014

(54) VISCOELASTIC GEL FOR DERMATOLOGICAL USE

(75) Inventor: Gilles Bos, Plan-les-Ouates (CH)

(73) Assignee: Anteis S.A., Plan-les-Ouates (CH)

( * ) Notice: Subject to any disclaimer, the term of this patent is extended or adjusted under 35 U.S.C. 154(b) by 1002 days.

(21) Appl. No.: 12/159,856

(22) PCT Filed: Jan. 5, 2007

(86) PCT No.: PCT/FR2007/000016
§ 371 (c)(1),
(2), (4) Date: Jul. 2, 2008

(87) PCT Pub. No.: WO2007/077399
PCT Pub. Date: Jul. 12, 2007

(65) Prior Publication Data
US 2011/0230438 A1 Sep. 22, 2011

(30) Foreign Application Priority Data
Jan. 6, 2006 (FR) ...................................... 06 00138

(51) Int. Cl.
*A61K 31/728* (2006.01)
(52) U.S. Cl.
CPC .................................... *A61K 31/728* (2013.01)
USPC .......................................... 514/54; 536/55.1
(58) Field of Classification Search
None
See application file for complete search history.

(56) References Cited

U.S. PATENT DOCUMENTS

| | | | |
|---|---|---|---|
| 5,106,615 A | 4/1992 | Dikstein et al. | |
| 5,906,997 A * | 5/1999 | Schwartz et al. | 514/781 |
| 7,060,287 B1 * | 6/2006 | Hubbard et al. | 424/423 |
| 2003/0034264 A1 * | 2/2003 | Hamai et al. | 206/364 |
| 2004/0185021 A1 | 9/2004 | Hubbard | |

FOREIGN PATENT DOCUMENTS

| | | |
|---|---|---|
| JP | 10306103 A | 11/1998 |
| JP | 2003507351 A | 2/2003 |
| WO | 0112247 A1 | 2/2001 |

OTHER PUBLICATIONS

English machine translation of Japanese patent publication H10-306103, downloaded from JPO website Mar. 19, 2013.*
Shimada et al., "Viscosity and Molecular Weight of Hyaluronic Acids" J. Biochem (1975) vol. 78 pp. 513-517.*
Japanese Office Action dated Jun. 20, 2012, from corresponding JP application.

* cited by examiner

*Primary Examiner* — Eric S Olson
(74) *Attorney, Agent, or Firm* — Young & Thompson

(57) ABSTRACT

The invention relates to a polysaccharide gel of natural origin for dermatological use that comprises an aqueous solution of the polysaccharide of 0.1 to 5% by weight/volume, for example hyaluronic acid, and a viscous and strongly hydrophilic biocompatible alcohol at 0.5-5% by weight/volume, for example glycerol, and optionally the adjuvants that are commonly used in dermatology. The gel is prepared by mixing the polysaccharide solution and the strongly hydrophilic viscous alcohol before sterilizing the entire mixture by, for example, moist heat.

5 Claims, 3 Drawing Sheets

Figure 1:
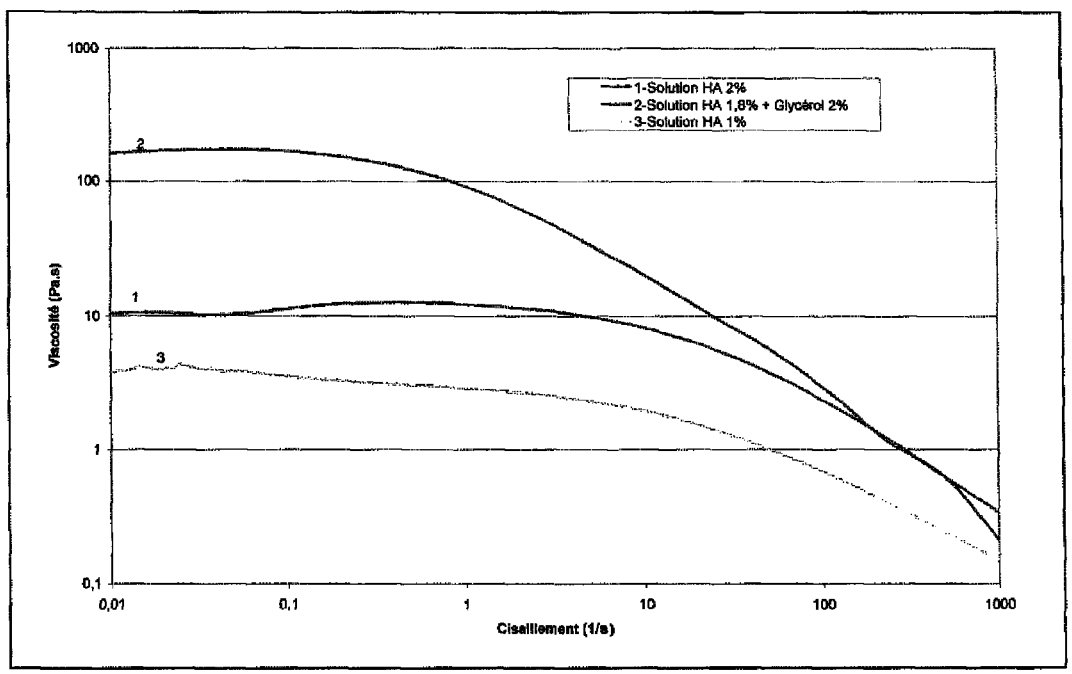

[Key to Fig. 1:]

Viscosité = Viscosity

Cisaillement = Shear

Glycérol = Glycerol

Figure 2:
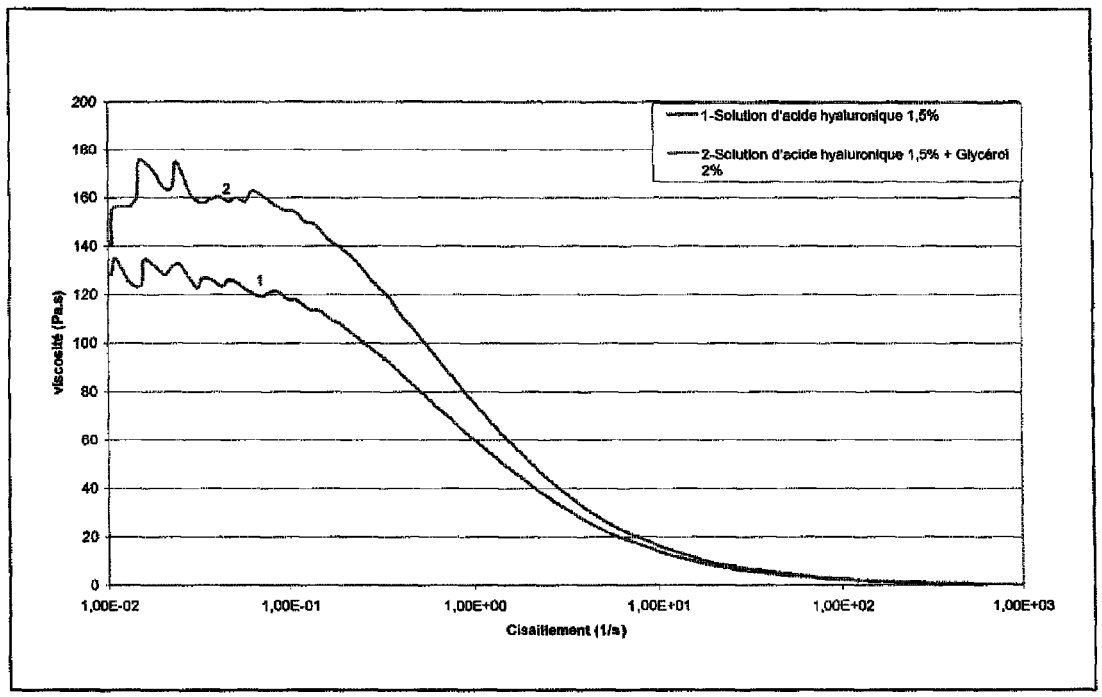

[Key to Fig. 2:]

Viscosité = Viscosity

Cisaillement = Shear

Solution d'acide hyaluronique 1,5% = Hyaluronic Acid Solution 1.5%

Glycérol = Glycerol

Figure 3:
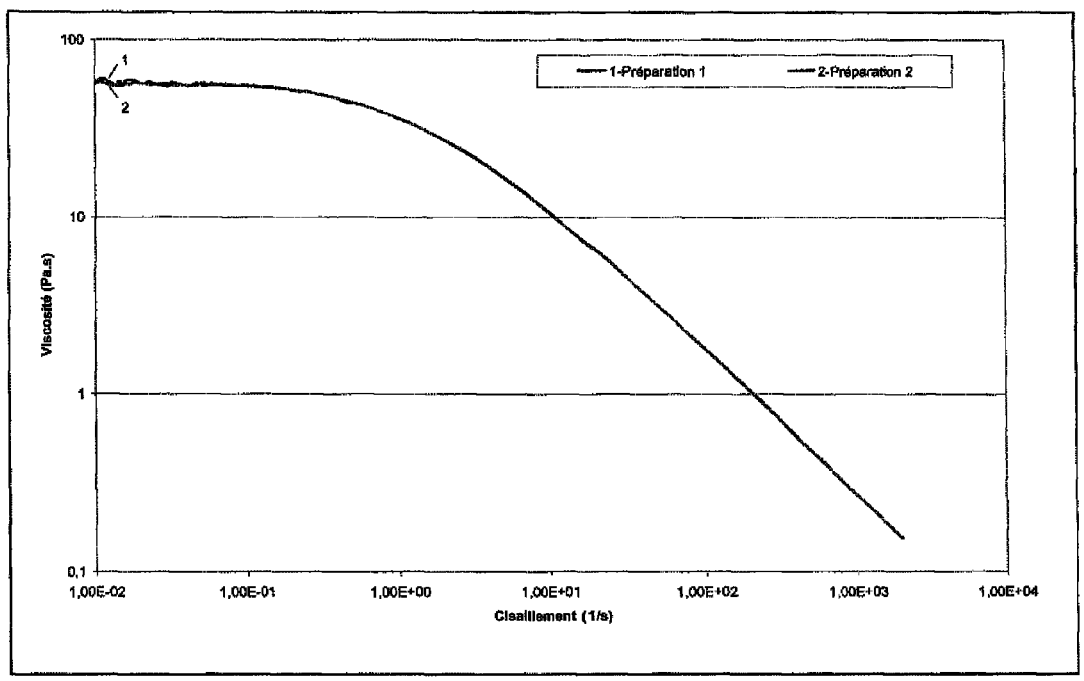

[Key to Fig. 3:]

Viscosité = Viscosity

Cisaillement = Shear

Préparation = Preparation

VISCOELASTIC GEL FOR DERMATOLOGICAL USE

The invention relates to a viscoelastic gel for dermatological use.

Various polymers of natural origin such as collagen, hyaluronic acid or cellulosic derivatives are frequently used in aesthetic medicine and in dermatology for filling in wrinkles, remodeling the face, increasing the volume of the lips, and rejuvenating the skin of the face; this last type of treatment is derived directly from mesotherapy.

For rejuvenating the skin, the practitioners frequently use hyaluronic acid, sometimes combined with complexes of vitamins, amino acids, mineral salts and nucleic acids.

The object of this invention consists of the combination of a polysaccharide of natural origin, more particularly hyaluronan, and a viscous alcohol so as to propose an injectable ready-to-use composition that optimizes the rejuvenation treatment of the skin, in particular that involves a polysaccharide gel of natural origin that is used as an injection in dermatology, comprising an aqueous polysaccharide solution at 0.1-5% by weight/volume and a viscous and strongly hydrophilic biocompatible alcohol at 0.5-5% by weight/volume, obtained by preparation of an aqueous solution of the polysaccharide and alcohol, then sterilization of this solution, and optionally the adjuvants that are commonly used in dermatology, sterilization after mixing the components having the effect of considerably increasing the viscosity of the resulting gel.

It has actually been found that the combination of a polysaccharide or its salts, in particular hyaluronan or sodium hyaluronate, and a small amount of a biocompatible viscous alcohol provides a composition whose viscosity greatly increases, and that when the biocompatible viscous alcohol is also hydrophilic, it considerably increases the water retention properties when the composition is injected under the skin that is to be treated.

Hydrophilic compound is defined as any compound that has a strong affinity for water. In an alcohol, the higher the density of OH groups, the more hydrophilic it is. For example, the glycerol, alcohol of low molecular weight (92.09 g.mol) and containing three OH groups, is extremely hydrophilic.

It has been found that the addition of a small amount, on the order of 0.5 to 5% by weight/volume, of a biocompatible viscous alcohol brings about a significant increase of the viscosity of a polysaccharide solution of natural origin at 0.1-5% by weight/volume, stabilizes this solution during the sterilization, and maintains particularly advantageous viscous properties for the rejuvenation of cutaneous tissue. The viscous alcohol can participate in the restructuring of the skin and the maturation of cells of this tissue and ensures the isotonicity of the mixture.

A biocompatible alcohol that has antiseptic properties, which reduces the risk of cutaneous infections, is preferably used. Actually, this risk is significant during a rejuvenation treatment, taking into account the large number of injections made in the face. Examples of such alcohols are in particular glycerol and polyethylene glycol lauryl sulfate.

Commercial hyaluronic acids have different molecular weights (MW) and different concentrations according to the manufacturer. By way of illustration, it is possible to use a concentration of 1.8% by weight/volume for hyaluronic acid of low to medium weight (0.5 to 1.8 MDa) and a concentration of 1.5% by weight/volume for hyaluronic acid of high weight (2.0 to 3.0 MDa).

The invention also provides a process for preparation of a polysaccharide gel of natural origin for dermatological use, comprising the stages consisting in:
a) Preparing an aqueous solution of polysaccharide and viscous and strongly hydrophilic biocompatible alcohol in the desired proportions,
b) Sterilizing the resulting solution, in particular by moist heat, and
c) Optionally putting the gel into a ready-to-use form.

FIGS. 1 to 3 are graphs that show the viscosities of the compositions of Examples 1 and 2 according to the invention and Example 3 (for comparison).

EXAMPLE 1

Influence of the Hyaluronic Acid Concentration and the Presence of Glycerol on the Viscosity of Solutions for the Rejuvenation of the Face Three solutions based on the same hyaluronic acid that is characterized by a mean molecular weight of 1.6 MDa were prepared.

The first solution is a hyaluronic acid solution at 1%.

The second solution is a solution of the same hyaluronic acid, but concentrated at 2%.

The third solution contains only 1.8% of this same hyaluronic acid to which glycerol was added at 2% by weight/volume.

The three preparations were sterilized by moist heat, then their rheological properties were analyzed using a rheometer by measuring the viscosity based on the shear rate imposed on the product.

It clearly appears that, according to the graph of FIG. 1, for the low shear rates (corresponding to those to which the preparation is exposed for the rejuvenation of cutaneous tissue after injection), the addition of glycerol to a hyaluronic acid solution has more influence for obtaining a high-viscosity preparation than the increase of the hyaluronic acid concentration.

EXAMPLE 2

Influence of Glycerol on the Viscosity of Hyaluronic Acid Solutions with High Molecular Weight Two solutions based on hyaluronic acid, characterized by a very high mean molecular weight (2.6 MDa), were prepared.

The first preparation is a hyaluronic acid solution at 1.5%.

The second preparation also contains 1.5% hyaluronic acid with high molecular weight to which was added glycerol at 2% by weight/volume.

The two preparations were sterilized by moist heat, then their rheological properties were analyzed using a rheometer by measuring the viscosity based on the shear rate imposed on the product.

The graph of FIG. 2 demonstrates that, even when the preparation consists of a hyaluronic acid of high molecular weight—therefore initially characterized by a high viscosity—the glycerol all the same tends to increase the viscous properties of the product.

EXAMPLE 3

Stabilization of the Preparation by Glycerol during the Sterilization (For Comparison)

A solution with 1.5% hyaluronic acid, characterized by a very high mean molecular weight (2.6 MDa), was prepared. This solution was then sterilized by moist heat (preparation 1).

Glycerol was added to several milliliters of this sterilized solution (preparation 2).

No rheological difference is observed between these two preparations; the graph of FIG. 3 and the examples presented above demonstrate the stabilizing effect of glycerol during sterilization.

It is therefore essential that the viscous alcohol be mixed with the hyaluronic acid solution before the sterilization to obtain the increase in viscosity.

After sterilization, the composition can be put into a ready-to-use form, for example in an ampoule or a flask that contains the dose to be injected by means of a syringe.

The composition can comprise adjuvants that are commonly used in dermatology, added to the mixture before sterilization. Such adjuvants are vitamins, mineral acids, mineral salts, and nucleic acids.

The invention claimed is:

1. A polysaccharide gel of natural origin that is used for injection in dermatology, comprising an aqueous solution containing 1.5-5% by weight/volume of hyaluronic acid of high MW 2.0 to 3.0 MDa, and glycerol at 0.5-5% by weight/volume, obtained by preparation of an aqueous solution of hyaluronic acid and the glycerol, then moist heat sterilization of this solution, and optionally adjuvants selected from the group consisting of vitamins, mineral acids, mineral salts, and nucleic acids, whereby the sterilization after mixing the components has the effect of appreciably increasing the viscosity of the resulting gel, compared to the gel without glycerol.

2. A polysaccharide gel of natural origin that is used for injection in dermatology, comprising an aqueous solution containing 1.8% by weight/volume of hyaluronic acid of mean MW of 0.5 to 1.8 MDa and 2% by weight/volume of glycerol, obtained by preparation of an aqueous solution of hyaluronic acid and the glycerol, then moist heat sterilization of this solution, and optionally adjuvants selected from the group consisting of vitamins, mineral acids, mineral salts, and nucleic acids, whereby the sterilization after mixing the components has the effect of appreciably increasing the viscosity of the resulting gel, compared to the gel without glycerol.

3. The gel according to claim 1, wherein the aqueous solution contains 1.5% by weight/volume of hyaluronic acid of high MW of 2.0 to 3.0 MDa and 2% by weight/volume of glycerol.

4. The process for preparation of a polysaccharide gel of natural origin for dermatological use according to claim 1, comprising the steps of:
   a) preparing an aqueous solution of hyaluronic acid and glycerol in the desired proportions,
   b) sterilizing the resulting solution, by moist heat, and
   c) optionally putting the gel into a ready-to-use form.

5. The gel according to claim 1, wherein the aqueous solution contains 1.5% to 5% by weight/volume of hyaluronic acid of high MW of 2.0 to 3.0 MDa and 0.5% to 2% by weight/volume of glycerol.

* * * * *

UNITED STATES PATENT AND TRADEMARK OFFICE
CERTIFICATE OF CORRECTION

PATENT NO.         : 8,685,944 B2                                      Page 1 of 1
APPLICATION NO. : 12/159856
DATED              : April 1, 2014
INVENTOR(S)        : Gilles Bos It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1141 days.

Signed and Sealed this

Twenty-ninth Day of September, 2015

Michelle K. Lee
*Director of the United States Patent and Trademark Office*